(12) United States Patent
Masoud (10) Patent No.: US 8,108,048 B2
(45) Date of Patent: Jan. 31, 2012

(54) PROTOCOL IMPLEMENTATION FOR TELEMETRY COMMUNICATIONS INVOLVING IMPLANTABLE MEDICAL DEVICES

(75) Inventor: Javaid Masoud, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 436 days.

(21) Appl. No.: 11/290,690

(22) Filed: Nov. 30, 2005

(65) Prior Publication Data

US 2007/0123946 A1 May 31, 2007

(51) Int. Cl.
*A61N 1/08* (2006.01)
(52) U.S. Cl. ........ 607/60; 607/32; 340/539.13; 128/903
(58) Field of Classification Search .................. 600/509; 607/30, 32, 59, 60, 56
See application file for complete search history.

(56) References Cited

U.S. PATENT DOCUMENTS

| | | | |
|---|---|---|---|
| 4,401,119 A | 8/1983 | Herpers | |
| 4,556,063 A | 12/1985 | Thompson et al. | |
| 5,314,450 A | 5/1994 | Thompson | |
| 5,331,966 A | 7/1994 | Bennett et al. | |
| 5,345,362 A | 9/1994 | Winkler | |
| 5,385,579 A | 1/1995 | Helland | |
| 5,564,434 A | 10/1996 | Halperin et al. | |
| 5,569,307 A * | 10/1996 | Schulman et al. | 607/56 |
| 5,626,620 A | 5/1997 | Kieval et al. | |
| 5,683,432 A * | 11/1997 | Goedeke et al. | 607/32 |
| 5,810,735 A | 9/1998 | Halperin et al. | |
| 5,843,139 A | 12/1998 | Goedeke et al. | |
| 5,931,857 A | 8/1999 | Prieve et al. | |
| 6,152,885 A | 11/2000 | Taepke | |
| 6,386,882 B1 * | 5/2002 | Linberg | 434/262 |
| 6,418,346 B1 * | 7/2002 | Nelson et al. | 607/59 |
| 6,443,891 B1 * | 9/2002 | Grevious | 600/302 |
| 6,539,253 B2 | 3/2003 | Thompson et al. | |
| 6,574,511 B2 * | 6/2003 | Lee | 607/60 |
| 6,577,893 B1 | 6/2003 | Besson et al. | |
| 6,804,558 B2 * | 10/2004 | Haller et al. | 607/30 |
| 2002/0032470 A1 | 3/2002 | Linberg | |
| 2002/0045920 A1 * | 4/2002 | Thompson | 607/60 |
| 2002/0095196 A1 * | 7/2002 | Linberg | 607/60 |
| 2004/0116981 A1 * | 6/2004 | Mazar | 607/60 |

(Continued)

FOREIGN PATENT DOCUMENTS

EP 0472411 A1 2/1992

(Continued)

OTHER PUBLICATIONS

Davis et al. "Performance of Slotted ALOHA Random Access with Delay Capture and Randomized Time of Arrival." IEEE Transactions on Communications. vol. COM-28, No. 5, May 1980.*

(Continued)

*Primary Examiner* — Carl H Layno
*Assistant Examiner* — Luther Behringer (57) ABSTRACT

Embodiments of the invention relate to optimizing telemetry communication involving one or more medical devices and one or more electrical devices. The telemetry communication is optimized by implementing software and/or one or more additional circuits within at least one medical device and at least one electrical device to provide one or more modes or functions of optimizing transfer of data between the medical device and the at least one electrical device, minimizing interference of the data transfer, and reducing data transfer time and/or preserving electrical energy sources of one or more of the medical device and the at least one electrical device.

21 Claims, 5 Drawing Sheets

U.S. PATENT DOCUMENTS

| | | |
|---|---|---|
| 2004/0127959 A1 | 7/2004 | Amundson et al. |
| 2005/0131493 A1 | 6/2005 | Boveja et al. |
| 2006/0161222 A1* | 7/2006 | Haubrich et al. ............... 607/60 |
| 2006/0161223 A1* | 7/2006 | Vallapureddy et al. ......... 607/60 |

FOREIGN PATENT DOCUMENTS

| | | |
|---|---|---|
| WO | 9722100 | 7/1997 |
| WO | 09802209 | 1/1998 |
| WO | 2002071305 A2 | 9/2002 |
| WO | WO 2007/065046 * | 6/2007 |

OTHER PUBLICATIONS

International Search Report for counterpart International Application No. PCT/US06/060609, mailed May 4, 2007.

* cited by examiner

PROTOCOL IMPLEMENTATION FOR TELEMETRY COMMUNICATIONS INVOLVING IMPLANTABLE MEDICAL DEVICES

FIELD OF THE INVENTION

The invention relates generally to implantable medical devices, and more particularly, to telemetry communications involving such implanted medical devices.

BACKGROUND OF THE INVENTION

Implantable medical devices (IMDs) are used to treat patients suffering from a variety of conditions. Examples of IMDs involving cardiac devices are implantable pacemakers and implantable cardioverter-defibrillators (ICDs). Such electronic medical devices generally monitor the electrical activity of the heart and provide electrical stimulation to one or more of the heart chambers when necessary. For example, pacemakers are designed to sense arrhythmias, i.e., disturbances in heart rhythm, and in turn, provide appropriate electrical stimulation pulses, at a controlled rate, to selected chambers of the heart in order to correct the arrhythmias and restore the proper heart rhythm. The types of arrhythmias that may be detected and corrected by IMDs include bradycardias (unusually slow heart rates), which can result in symptoms such as fatigue, dizziness, and fainting, and certain tachycardias (unusually fast heart rates), which can result in sudden cardiac death (SCD).

Implantable cardioverter-defibrillators (ICDs) also detect arrhythmias and provide appropriate electrical stimulation pulses to selected chambers of the heart to correct the abnormal heart rate. In contrast to pacemakers, however, an ICD can also provide pulses that are much stronger and less frequent. This is because ICDs are generally designed to correct fibrillation, which is a rapid, unsynchronized quivering of one or more heart chambers, and severe tachycardias, during which the heartbeats are very fast but coordinated. To correct such arrhythmias, ICDs deliver low, moderate, or high-energy shocks to the heart.

Generally, IMDs are equipped with an on-board memory in which telemetered signals can be stored for later retrieval and analysis. In addition, a growing class of cardiac medical devices, including implantable heart failure monitors, implantable event monitors, cardiovascular monitors, and therapy devices, can be used to provide similar stored device information. Typically, the telemetered signals can provide patient physiologic and cardiac information. This information is generally recorded on a per heartbeat, binned average basis, or derived basis, and involve, for example, atrial electrical activity, ventricular electrical activity, minute ventilation, patient activity score, cardiac output score, mixed venous oxygen score, cardiovascular pressure measures, time of day, and any interventions and the relative success of such interventions. Telemetered signals can also be stored in a broader class of monitors and therapeutic devices for other areas of medicine, including metabolism, endocrinology, hematology, neurology, muscular disorders, gastroenterology, urology, ophthalmology, otolaryngology, orthopedics, and similar medical subspecialties.

Generally, upon detecting arrhythmias and, when necessary, providing corresponding therapies to correct such arrhythmias, the IMDs store the telemetered signals over a set period of time (usually before, during, and after the occurrence of such arrhythmic event). Current practice in the art involves the use of an external communication unit, e.g., an external programmer, for non-invasive communication with IMDs via uplink and downlink communication channels associated with the communication device. In accordance with conventional medical device programming systems, a programming head can be used for facilitating two-way communication between IMDs and the external communication device. In many known implanted IMD systems, the programming head can be positioned on the patient's body over the IMD side site such that one or more antennae within the head can send RF signals to, and receive RF signals from, one or more antennae disposed within the hermetic enclosure of the IMD or disposed within the connector block of the IMD in accordance with common practice in the art.

Implementation and operation of most, if not all, RF communication systems for IMDs and external communication devices involves a balancing or compromising of certain countervailing considerations, relating to such interrelated operational parameters as data transmission rate and transmission range, among numerous others. Such operational parameters are often interrelated in the sense that the adjustment of one operating parameter may permit or require the adjustment of one or more other operating parameters even while predetermined system performance goals and/or requirements continue to be met and predetermined limitations imposed upon operational parameter adjustment are adhered to. One example of this is the trade-off between signal range and signal power. Simply stated, for a given communication scheme, a more powerful (e.g., higher amplitude) signal has a longer effective range. Thus, decreasing the range of a communication link (e.g., reducing the distance between transmitters and receivers in the link) allows the transmission power to be decreased, while other operational parameters, e.g., data transmission rate, can be held at a constant value.

Another example is the trade-off between data transmission rate and transmitted signal power. Those of ordinary skill in the art will appreciate that in most instances, increasing the data transmission rate over an RF channel typically requires increased signal bandwidth. Increasing the bandwidth, in RF, tends to lead to increased power consumption by the communication system in order to maintain an acceptable signal-to-noise ratio.

Still another example of the trade-offs associated with the operational parameters, and system performance goals of an RF communication system is associated with data transmission rate versus signal range. As noted above, increasing data transmission rate typically results in an increased bandwidth of the transmitted signals; conversely, decreasing data transmission rate typically reduces signal bandwidth. If bandwidth can be reduced, the range of operation can be increased for a given level of power consumption.

As noted above, the foregoing and other trade-offs associated with various operational parameters of a communication system arise in most applications involving RF transmission and reception. However, the nature of the interrelation between the various operational parameters may vary depending, for example, upon the type of modulation used (e.g., pulse position modulation, frequency shift keying, frequency modulation, amplitude modulation, etc.), as well as upon the type of coding used. In the context of IMD systems, there are additional considerations that must be addressed. Primary among these are reliability of transmission and reception, and conservation of implanted device power. Conservation of implanted device power (which in most cases implies minimization of current drain upon an implanted device's internal battery) in particular renders the aforementioned trade-offs—rate-versus-range, range-versus-power, rate-versus-power, as well as others—highly significant. In most cases, however, the settings of operational parameters of interest are static, or if adjustable, are adjusted simply using a single parameter.

SUMMARY OF THE INVENTION

Embodiments of the invention relate to optimizing telemetry communication involving one or more medical devices and one or more electrical devices. The telemetry communication is optimized by implementing software and/or one or more additional circuits within at least one medical device and at least one electrical device to provide one or more modes or functions of optimizing transfer of data between the medical device and the at least one electrical device, minimizing interference of the data transfer, and reducing data transfer time and/or preserving electrical energy sources of one or more of the medical device and the at least one electrical device.

In some embodiments, a system for optimizing telemetry communication involving one or more medical devices is provided. The system comprises a medical device, one or more electrical devices, and circuitry within one or more of the medical device and at least one of the one or more electrical devices. The medical device is implanted in a patient, and has a unit including one or more of a transmitter and a receiver, wherein the medical device unit is configured for enabling telemetry communications involving the medical device. The at least one electrical device has a unit including one or more of a transmitter and a receiver, wherein each electrical device unit is configured for enabling telemetry communications between the at least one electrical device and the medical device. The circuitry is configured to implement one or more modes of protocol for telemetry communications between the at least one electrical device and the medical device. The one or more modes of protocol are configured to provide one or more of optimizing transfer of data between the medical device and the at least one electrical device, minimizing interference of the data transfer, and preserving electrical energy sources of one or more of the medical device and the at least one electrical device.

In some embodiments, a system for optimizing telemetry communication involving one or more medical devices is provided. The system comprises a medical device, one or more electrical devices, and circuitry within one or more of the medical device and at least one of the one or more electrical devices. The medical device is implanted in a patient, and has a unit including one or more of a transmitter and a receiver, wherein the medical device unit is configured for enabling telemetry communications involving the medical device. The at least one electrical device has a unit including one or more of a transmitter and a receiver, wherein each electrical device unit is configured for enabling telemetry communications between the at least one electrical device and the medical device. The circuitry is configured to provide one or more functions of optimizing transfer of data between the medical device and the at least one electrical device, minimizing interference of the data transfer, and preserving electrical energy sources of one or more of the medical device and the at least one electrical device.

In other embodiments, a method of optimizing telemetry communication between one or more medical devices is provided. The method comprises providing a medical device implanted in a patient, where the medical device has a unit including one or more of a transmitter and a receiver, wherein the medical device unit is configured for enabling telemetry communications involving the medical device. The method comprises providing one or more electrical devices with at least one of the one or more electrical devices has a unit including one or more of a transmitter and a receiver, wherein each electrical device unit is configured for enabling telemetry communications between the at least one electrical device and the medical device. The method comprises providing circuitry within one or more of the medical device and the at least one electrical device, where the circuitry is configured to implement one or more modes of protocol for the telemetry communications between the at least one electrical device and the medical device. The one or modes of protocol are configured to provide optomized transfer of data between the medical device and the at least one electrical device, minimizing interference of the data transfer, and preserving electrical energy sources of the medical device and the at least one electrical device.

DETAILED DESCRIPTION OF THE PREFERRED EMBODIMENTS

The following discussion is presented to enable a person skilled in the art to make and use the present teachings. Various modifications to the illustrated embodiments will be readily apparent to those skilled in the art, and the generic principles herein may be applied to other embodiments and applications without departing from the present teachings. Thus, the present teachings are not intended to be limited to the embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the present teachings. Skilled artisans will recognize the examples provided herein have many useful alternatives and fall within the scope of the present teachings.

The embodiments of the present invention can be implemented with any IMD having RF telemetry capabilities. At present, a wide variety of IMDs are commercially available or proposed for clinical implantation. Such IMDs include pacemakers as well as ICDs, drug delivery pumps, cardiomyostimulators, cardiac and other physiologic monitors, nerve and muscle stimulators, deep brain stimulators, cochlear implants, and artificial organs (e.g., such as artificial hearts). In addition, as the technology advances, it is contemplated that IMDs shall become even more complex with respect to programmable operating modes, menus of operating parameters, and monitoring capabilities of increasing varieties of physiologic conditions and electrical signals. It is to be appreciated that embodiments of the present invention will be applicable in such emerging IMD technology as well. Further, the embodiments of the invention can be implemented in more than one IMD implanted within the same patient to enable telemetry communication between the IMDs.

Figure 1:
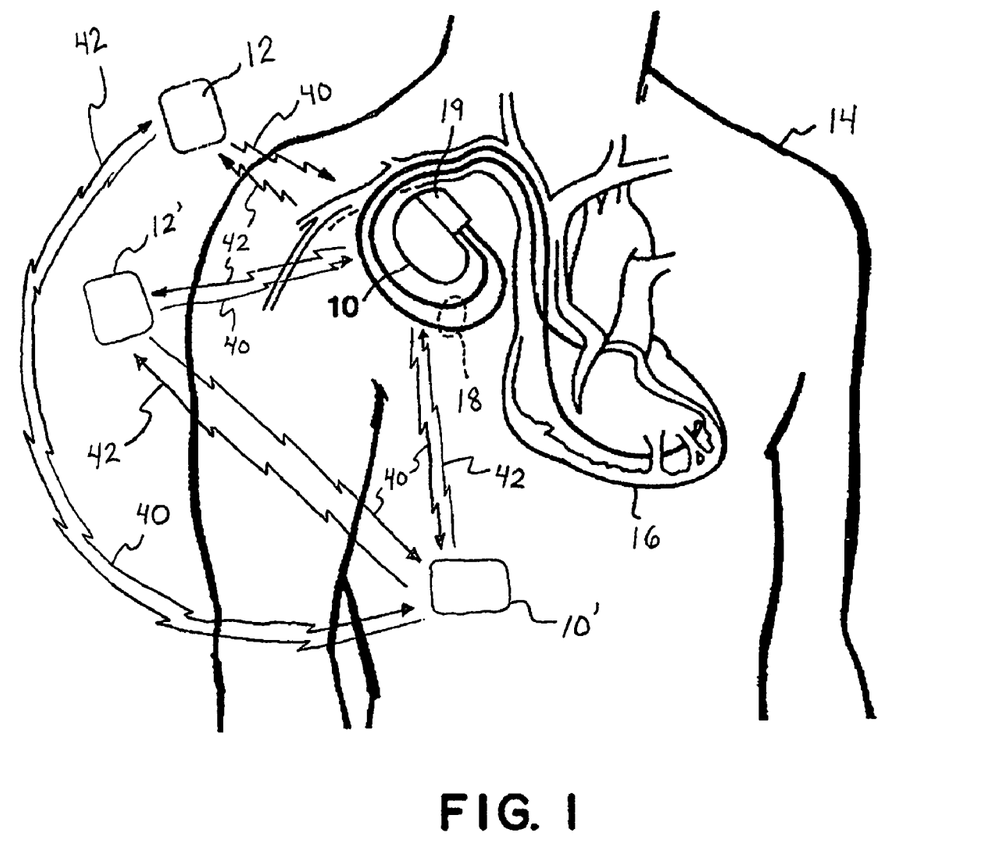
FIG. 1 is an illustration of a system including an implantable medical device in accordance with certain embodiments of the invention.

FIG. 1 illustrates bi-directional telemetry communication involving one or more IMDs in accordance with certain embodiments of the invention. In certain embodiments, as shown, telemetry communications 40 and 42 (as described herein) can take place between an IMD 10 and any number of electrical devices. In certain embodiments, the electrical devices can include one or more of at least one implantable medical instrumentation and of at least one external communication device. As shown in FIG. 1, in certain embodiments, the at least one implantable medical instrumentation can include IMD 10' and the at least one external communication device can include external communication devices 12 and 12'; however, it is to be appreciated that such quantities are simply exemplary and not provided to limit the invention. While embodiments may be generally described herein involving telemetry communications 40, 42 between the IMD 10 and the external communication device 12 (with respect to FIGS. 2 through 5), it is to be appreciated that the invention, as shown, is equally applicable in embodiments in which such telemetry communications occur between the IMD 10 and any other electrical devices (e.g., the IMD 10' and/or the external communication device 12'). Further, it is to be appreciated that the invention, as shown, is equally applicable in embodiments in which telemetry communications occur between the IMD 10' and other IMDs and/or other electrical devices (e.g., the IMD 10' and/or one or more of the external communication devices 12, 12').

In certain embodiments, when the IMD 10 is used for cardiac applications (e.g., to provide cardiac sensing and pacing functions for a patient), the IMD 10 can be a cardiac device; for example, a pacemaker, an ICD, a hemodynamic monitor, etc.; however, as described above, neither the IMD 10 (nor the IMD 10' or any other IMDs similarly implanted in patient 14) should be limited to such applications or such devices. The IMDs 10, 10' are implanted in the same patient 14 subcutaneously or submuscularly and, in certain embodiments, can be typically oriented to the skin surface. In certain embodiments, when the IMD 10 is used for cardiac applications, as shown, the IMD 10 is electrically coupled to heart 16 of the patient 14 through pace/sense or cardioversion/defibrillation electrodes operatively coupled to lead conductor(s) of one or more endocardial leads 18, which in turn, are coupled to a connector block 19 of the IMD 10 in a manner well known in the art.

As generally mentioned above, among other design functions, each of the external communication devices 12 and 12' is designed for non-invasive communication with one or more of the IMD 10 and IMD 10', where such communication is enabled via downlink and uplink communication channels, which will be further described below. In certain embodiments, one or more of the external communication devices 12, 12' can be an external pressure reference monitor (EPR). An EPR is typically used to derive reference pressure data for use in combination with absolute pressure derived from an IMD. In addition, an EPR measures and records barometric pressure which is necessary for correlation to atmospheric pressure. However, it is to be appreciated that the invention should not be limited to such. Generally, any form of portable programmer, interrogator, recorder, monitor, or telemetered signals transmitter and/or receiver found suitable for communicating with the IMD 10 and/or the IMD 10', in turn, could be used for the external communication devices 12, 12'.

Figure 2:
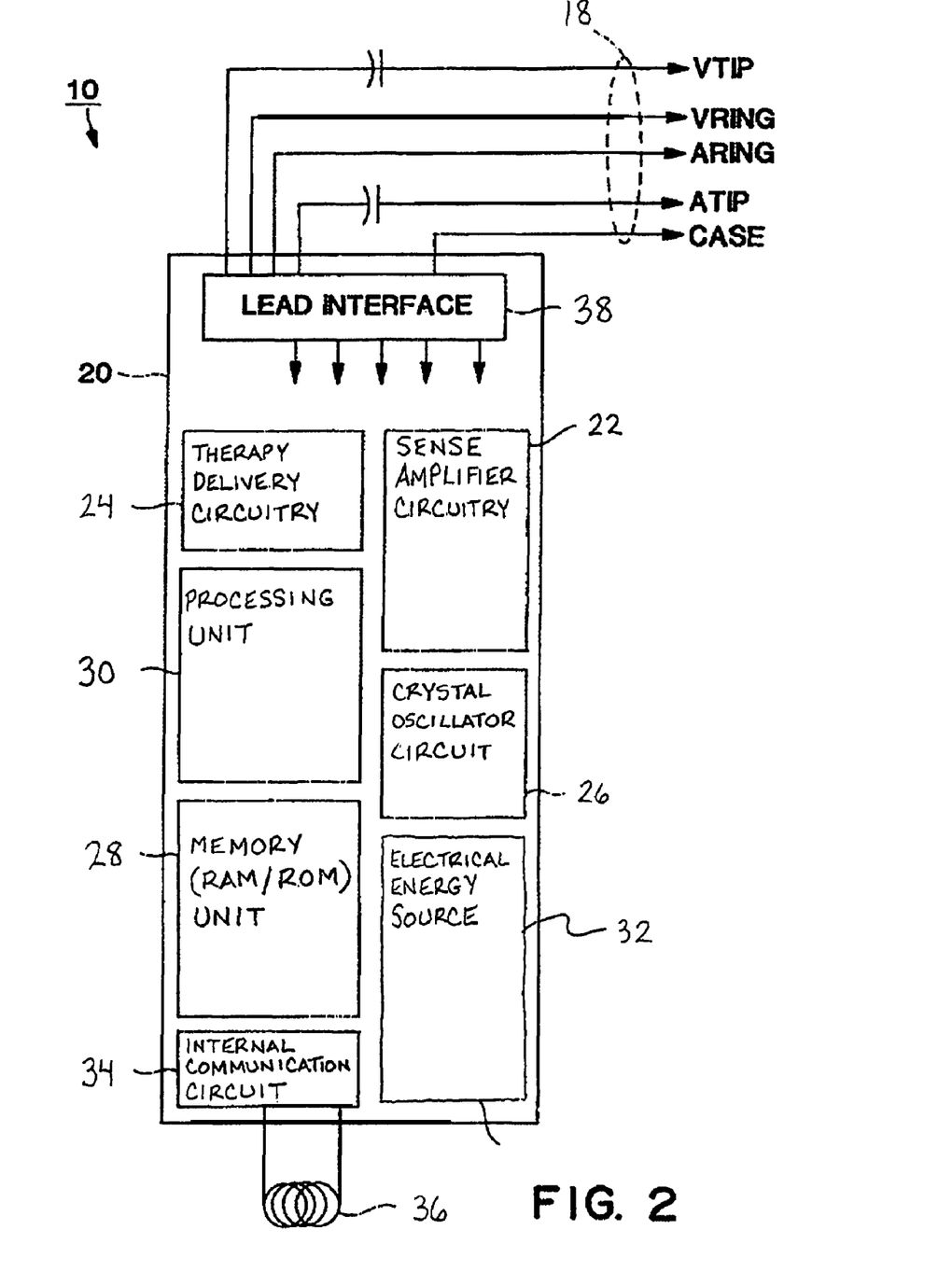
FIG. 2 is a block diagram of exemplary circuitry of the implantable medical device of FIG. 1.

FIG. 2 shows an exemplary block diagram of the electronic circuitry of the IMD 10 in accordance with certain embodiments of the invention. While FIG. 2 specifically references the IMD 10, it is to be appreciated that, in certain embodiments, the IMD 10' (and any other IMDs implanted in the patient 14) can be similarly configured. As can be seen from FIG. 2, the IMD 10 includes primary circuitry 20 for managing the device's functioning, with such primary circuitry 20 being contained within a hermetic enclosure of the IMD 10. The primary circuitry 20 includes a number of electrical components, most of which are exemplified in published U.S. patent application Ser. No. 09/729,845, entitled "Implantable medical device incorporating integrated circuit notch filters", which patent application is incorporated herein by reference in relevant part. In certain embodiments, the primary circuitry 20 in FIG. 2 includes sense amplifier circuitry 22, therapy delivery circuitry 24, a crystal oscillator circuit 26, a random-access memory and read-only memory (RAM/ROM) unit 28, a processing unit 30, and an electrical energy source 32. In certain embodiments, the primary circuitry 20 also includes an internal communication circuit 34 and one or more antennae 36 so that the IMD 10 is capable of communicating with the external communication device 12. It should be appreciated that the below descriptions of the primary circuitry 20 within the IMD 10 are merely exemplary configurations.

In certain embodiments, when the IMD 10 is used for cardiac applications (e.g., to provide cardiac sensing and pacing functions for the patient 14), the IMD 10 is coupled to the one or more endocardial leads 18 which, when implanted, extend transvenously between the implant site of the IMD 10 and the patient's heart 14, as previously noted with reference to FIG. 1. As mentioned above, the physical connections between the leads 18 and the various internal components of IMD 10 are facilitated by means of a conventional connector block assembly 19. Electrically, the coupling of the conductors of the leads 18 and internal electrical components of IMD 10 may be facilitated by means of a lead interface circuit 38 which functions, in a multiplexer-like manner, to selectively and dynamically establish necessary connections between various conductors in the leads 18 and individual electrical components of the IMD 10, as would be familiar to those of ordinary skill in the art. In certain embodiments, with respect to such cardiac applications, the various conductors in the leads 18 can include atrial tip and ring electrode conductors, $A_{tip}$ and $A_{ring}$, and ventricular tip and ring electrode conductors, $V_{tip}$ and $V_{ring}$. For the sake of clarity, the specific connections between the leads 18 and the various components of the IMD 10 are not shown in FIG. 2, although such connections will be familiar to those of ordinary skill in the art. For example, in cardiac applications, the leads 18 will necessarily be coupled, either directly or indirectly, to the sense amplifier circuitry 22 and the therapy delivery circuitry 24, in accordance with common practice, such that cardiac electrical signals may be conveyed to the sense amplifier circuitry 22 and such that stimulating pulses may be delivered by the therapy delivery circuitry 24 to cardiac tissue, via the leads 18. Also not shown in FIG. 2 is the protection circuitry commonly included in implanted devices to protect, for example, the sensing circuitry of the device from high voltage stimulating pulses.

As previously noted, the primary circuitry 20 includes the processing unit 30 which generally varies in sophistication and complexity depending upon the type and functional features of the IMD 10. In certain embodiments, the processing unit 30 can be an off-the-shelf programmable microprocessor, a microcontroller, a custom integrated circuit, or any of a wide variety of other implementations generally known.

Although specific connections between the processing unit 30 and other components of the stimulation control circuit 20 are not shown in FIG. 2, it will be apparent to those of ordinary skill in the art that the processing unit 30 functions to control the timed operation of the sense amplifier circuitry 22 and the therapy delivery circuitry 24. In certain embodiments, the functioning of the processing unit 30 would be under control of firmware and programmed software algorithms stored in RAM and ROM including PROM and/or reprogrammable ROM and are carried out using a processing unit of a typical microprocessor core architecture. In certain embodiments, the processing unit 30 can also include a watchdog circuit, a DMA controller, a lock mover/reader, a CRC calculator, and other specific logic circuitry coupled together by on-chip bus, address bus, and power, clock, and control signal lines in paths or trees in a manner well known in the art.

In certain embodiments, as is known in the art, the electrical energy source 32 powers the primary circuitry 20 and can also be used to power any electromechanical devices, e.g., valves, pumps, etc. of a substance delivery IMD, or to provide electrical stimulation energy of an ICD shock generator, cardiac pacing pulse generator, or other electrical stimulation generator. In certain embodiments, the electrical energy source 32 is a high energy density, low voltage battery coupled with a power supply/POR circuit having power-on-reset (POR) capability. The power supply/POR circuit provides one or more low voltage power $V_{lo}$, the POR signal, one or more $V_{REF}$ sources, current sources, an elective replacement indicator (ERI) signal, and, in the case of an ICD, high voltage power $V_{hi}$ to the therapy delivery circuitry 24. For the sake of clarity in exemplary block diagram provided in FIG. 2, the connections between the electrical energy source 32 and the electrical components of the IMD 10 are not shown, as one skilled in the art would be familiar with such connections.

In certain embodiments, the sense amplifier circuitry 22 can be configured to process physiologic signals that are used to trigger or modulate therapy delivery and are stored as physiologic signal data for later retrieval as described herein. Generally, the sense amplifier circuitry 22 is coupled to electrical signal sense electrodes and/or physiologic sensors on or in the housing of the IMD 10 or as mentioned above, situated at sites distanced from the IMD housing, typically in distal portions of the elongated leads 18. As is generally known, the sensors or electrodes located outside the housing are coupled by conductors to feedthrough pins of feedthroughs extending through the housing wall. Certain physiologic sensors or sense electrodes can be mounted to a connector assembly so that the conductors are quite short.

In certain embodiments, the conductors include the elongated conductors of the leads 18 extending to the remotely situated physiologic sensors and sense electrodes. As such, in some cardiac applications, the sense amplifier circuitry 22 is designed to receive electrical cardiac signals from the leads 18 and to process such signals to derive event signals reflecting the occurrence of specific cardiac electrical events, including atrial contractions (P-waves) and ventricular contractions (R-waves). These event-indicating signals are provided to the processing unit 30 for use by the unit 30 in controlling the synchronous stimulating operations of the IMD 10 in accordance with common practice in the art. In addition, these event indicating signals may be communicated, via uplink transmission, to the external communication device 12.

In certain embodiments, the therapy delivery circuitry 24 can be configured to deliver electrical stimulation to the patient 14, e.g., cardioversion/defibrillation shocks and/or cardiac pacing pulses delivered to the heart 16, or other electrical stimulation delivered to the brain, other organs, selected nerves, the spinal column, the cochlea, or muscle groups, including skeletal muscle wrapped about the heart. Alternatively, in certain embodiments, the therapy delivery circuitry 24 can be configured as a drug pump delivering drugs into organs for therapeutic treatment or into the spinal column for pain relief. Alternatively, in certain embodiments, the therapy delivery circuitry 24 can be configured to operate an implantable heart assist device or pump implanted in patients awaiting a heart transplant operation.

In certain embodiments, when the IMD 10 is used for cardiac applications, the sense amplifier circuitry 22 also includes patient activity sensors or other physiologic sensors for sensing the need for cardiac output and modulating pacing parameters accordingly through many alternative approaches set forth in the prior art. If the IMD 10 is an ICD, the therapy delivery circuitry 24 generally includes one or more high power cardioversion/defibrillation output capacitors, electronic circuitry coupled to the sense amplifiers for detecting and discriminating pathologic and/or nonpathologic arrhythmias from one another and providing other functions, high voltage electronic circuitry for charging the output capacitor(s) from a battery voltage to a higher voltage, and electronic switching circuitry for dumping the charge built up on the output capacitor(s) through the cardioversion/defibrillation electrodes operatively coupled to the one or more endocardial leads 18. Such IMDs are described in detail in U.S. Pat. Nos. 5,626,620 or 5,931,857, respectively, which patents are incorporated herein by reference in their relevant parts.

Registers of the memory unit 28 can be used for storing data compiled from sensed cardiac activity and/or relating to device operating history or sensed physiologic parameters. Generally, the data storage can be triggered manually by the patient 14, on a periodic basis, or by detection logic (e.g., within the sense amplifier circuitry 22) upon satisfaction of certain programmed-in event detection criteria. If not manually triggered, in certain embodiments, the criteria for triggering data storage within the IMD 10 is programmed via telemetry transmitted instructions and parameter values. If manually triggered, in some cases, the IMD 10 includes a magnetic field sensitive switch that closes in response to a magnetic field, and the closure causes a magnetic switch circuit to issue a switch closed (SC) signal to the processing unit 30 which responds in a "magnet mode". For example, the patient 14 may be provided with a magnet (e.g., incorporated with the external communication device 12) that can be applied over the IMD 10 to close the switch and prompt the processing unit 30 to store physiologic episode data when the patient experiences certain symptoms and/or deliver a therapy to the patient 14. Following such triggering, in certain embodiments, event related data, e.g., the date and time, may be stored along with the stored periodically collected or patient initiated physiologic data. Typically, once stored, the data is ready for telemetry transmission on receipt of a retrieval or interrogation instruction.

In certain embodiments, the crystal oscillator circuit 26 generally employs clocked CMOS digital logic ICs requiring a clock signal provided by a crystal (e.g., piezoelectric) and system clock coupled thereto as well as discrete components, e.g., inductors, capacitors, transformers, high voltage protection diodes, and the like that are mounted with the ICs to one or more substrate or printed circuit board. Typically, each clock signal generated by the system clock is routed to all applicable clocked logic via a clock tree. In certain embodiments, the system clock provides one or more fixed frequency clock signals that are independent of the battery voltage over an operating battery voltage range for system timing and control functions and in formatting telemetry signal transmissions. Again, the lines over which such clocking signals are provided to the various timed components of the IMD 10 (e.g., processing unit 32) are omitted from FIG. 2 for the sake of clarity.

Those of ordinary skill in the art will appreciate that IMD 10 may include numerous other components and subsystems, for example, activity sensors and associated circuitry. The presence or absence of such additional components in IMD 10, however, is not believed to be pertinent to the present invention, which relates to the implementation and operation of a communication subsystem in the IMD 10, and associated communication subsystems in one or more of further implantable medical instrumentation (e.g., IMD 10') and other electrical devices (e.g., external communication devices 12 and 12').

In certain embodiments, the IMD 10 can involve an implantable cardiac monitor without therapy delivery system 24, e.g., an implantable EGM monitor for recording the cardiac electrogram from electrodes remote from the heart as disclosed in U.S. Pat. No. 5,331,966 and PCT publication WO 98/02209, which patent is incorporated herein by reference in its relevant part. Alternatively, the IMD 10 can involve an implantable hemodynamic monitor (IHM) for recording cardiac electrogram and other physiologic sensor derived signals, e.g., one or more of blood pressure, blood gases, temperature, electrical impedance of the heart and/or chest, and patient activity. The Medtronic® REVEAL® Insertable Loop Recorder, having EGM electrodes spaced across its housing, is an example of the former, and the Medtronic® CHRONICLES IHM, coupled with a capacitive pressure and temperature sensing lead and EGM sense electrodes of the type described in U.S. Pat. No. 5,564,434, which patent is incorporated herein by reference in its relevant part, is an example of the latter.

As described above, the IMD 10 includes an internal communication circuit 34 and one or more antennae 36. In certain embodiments, each of the antennae 36 are mounted to the IMD 10 in one or more of a wide variety of configurations. For example, one or more of the IMD antennae 36 can take the form of a surface mounted antenna (e.g., as described in U.S. Pat. No. 4,401,119, which patent is incorporated herein by reference in its relevant part), or one or more of the antennae 36 can be enclosed within or mounted to the IMD connector block assembly. However, it is to be appreciated that the invention should not be limited to such. It is desirable to reduce the size of the IMD while increasing its functional capabilities and prolonging battery life to increase longevity. In accordance with certain embodiments, the current consumption of certain transceiver circuits can also be decreased to accomplish that goal. By way of background, the IMD telemetry system and functions are described as follows. For convenience of description, the embodiments described as follows use short range RF downlink telemetry transmissions 40 and uplink telemetry transmissions 42, but it should be appreciated that the embodiments of the invention should not be limited to such. Similarly, the terms "telemeter", "telemetry transmission" and the like are intended to embrace any such action and manner of communicating and conveying data and commands between the IMD 10 and other electrical devices (e.g., IMD 10', external communication devices 12 and/or 12', and any external monitoring device) in the uplink transmission direction and the downlink transmission direction.

In the IMD 10, uplink and downlink telemetry capabilities are provided to enable communication with one or more external electrical devices (e.g., one or more of the external communication devices 12, 12'), a more proximal medical device on the patient's body, or other implantable medical instrumentation (e.g., IMD 10') in the patient's body. Generally, the stored physiologic data as well as one or more of real-time generated physiologic data and non-physiologic data (collectively referred to herein as "patient data") can be transmitted by uplink RF telemetry from the IMD 10 to the other devices or instrumentation in response to a downlink telemetered interrogation command, events within the IMD 10 or patient 14, magnet swipe across the IMD 10 by the patient 14, upon satisfaction of certain programmed-in event detection criteria and/or timed events. The real-time physiologic data can include real time sampled signal levels, e.g., intracardiac electrocardiogram amplitude values, and sensor output signals. The non-physiologic patient data can include currently programmed device operating modes and parameter values, battery condition, device ID, patient ID, implantation dates, device programming history, real time event markers, and the like. In the context of implantable pacemakers and ICDs, such patient data can include programmed sense amplifier sensitivity, pacing or cardioversion pulse amplitude, energy, and pulse width, pacing or cardioversion lead impedance, programmed setting, and/or accumulated statistics related to device performance, e.g., data related to detected arrhythmia episodes and applied therapies.

Figure 3:
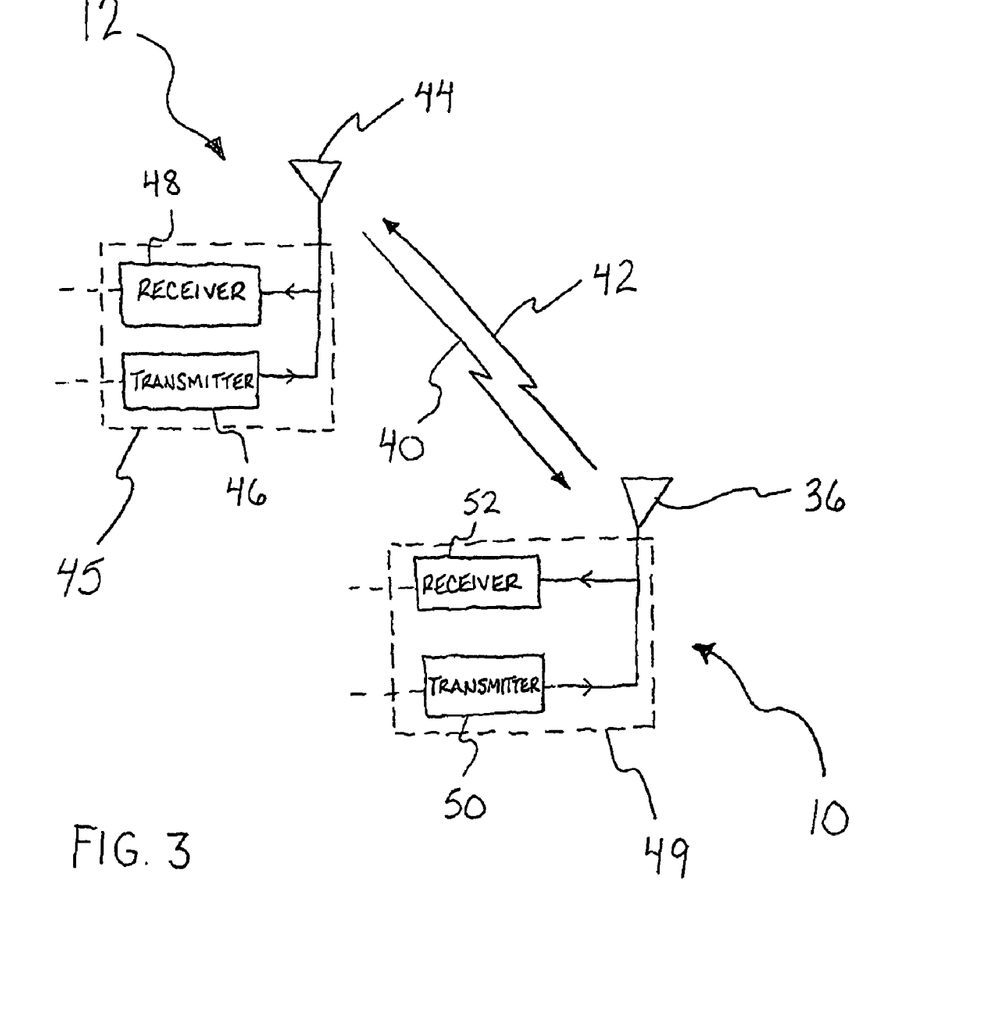
FIG. 3 is a block diagram of exemplary units implemented in the implantable medical device of FIG. 1 and in an external communication device.

With respect to FIG. 3, in certain embodiments, programming commands or patient data can be transmitted between the one or more IMD antennae 36 associated with the IMD 10 and one or more antennae 44 associated with the external communication device 12. In certain embodiments, a high frequency signal can be employed. As such, it would not be necessary for the external communication device antenna 44 to be contained in an external communication device RF head so that it can be located close to the patient's skin overlying the IMD 10. Instead, the external communication device antenna 44 can be located on the case of the external communication device 12 some distance, e.g., a few meters, from the IMD 10 in the patient 14. For example, the external communication device 12 and external communication device antenna 44 may be on a stand a few meters or so away from the patient 14 as described, for example, in the above-referenced '119 patent and in U.S. Pat. Nos. 5,683,432 and 5,843,139, which patents are incorporated herein by reference in their relevant parts. Moreover, the patient 14 may be active and could be exercising on a treadmill or the like during a telemetry interrogation and transmission of real time ECG or physiologic parameters. The external communication device 12 may also be designed to universally program existing IMDs that employ the conventional ferrite core, wire coil, RF telemetry antenna of the prior art and therefore also have a conventional external communication device RF head and associated software for selective use with such IMDs.

In an uplink telemetry transmission 42, the external communication device antenna 44 operates as a telemetry receiver antenna, and the IMD antenna 36 operates as a telemetry transmitter antenna. Conversely, in a downlink telemetry transmission 40, the communication device antenna 44 operates as a telemetry transmitter antenna, and the IMD antenna 36 operates as a telemetry receiver antenna. As shown with respect to FIG. 1, such telemetry transmissions 42, 40 are also referenced between the IMD 10 and the IMD 10', between IMD 10 and external communication device 12', and between IMD 10' and external communication device 12. As such, it is to be appreciated that IMD 10' and external communication device 12' can be similarly configured as described herein with respect to IMD 10 and external communication device 12 respectively, to facilitate bi-directional telemetry communications therewith.

In certain embodiments, the antenna 44 within the external communication device 12 is electrically coupled to a telemetry transceiver 45, e.g., comprising a telemetry transmitter 46 and telemetry receiver 48. Similarly, in certain embodiments, the IMD antenna 36 is coupled to a telemetry transceiver 49 comprising a telemetry transmitter 50 and telemetry receiver 52, which are located within the internal communications circuit 34 of the IMD 10. In certain embodiments, the communication device and IMD telemetry transmitters, 46 and 50 respectively, and the communication device and IMD telemetry receivers, 48 and 52 respectively, can be coupled to control circuitry and registers under the control of a microcomputer and software, for example, as described in U.S. Pat. Nos. 5,843,139 or U.S. Pat. No. 5,683,432, which patents are incorporated herein by reference in their relevant parts.

In an uplink telemetry transmission 42, the telemetered data can be encoded in any of a wide variety of telemetry formats. While not being limited to such, some examples of particular data encoding or modulation types and/or techniques that can be utilized with such uplink transmissions include noise modulation, general spread spectrum encoding, bi-phase encoding, Frequency Shift Key (FSK), Time Division Multiple Access (TDMA), pre-emphasis/de-emphasis of baseband, vestigial, Code Division Multiple Access (CDMA), Quadrature Amplitude Modulation (QAM), pi/8, Quad-QAM, 256-QAM, 16-QAM, delta modulation, Phase Shift Key (PSK), Quadrature Phase Shift Keying (QPSK), Quadrature Amplitude Shift Keying (QASK), minimum shift keying, Tamed Frequency Modulation (TFM), Orthogonal Frequency Division Multiplexing (OFDM), the BLUETOOTH communication protocol, any 802.11 modulation configuration, Worldwide Interoperability for Microwave Access (WiMAX), any 802.16 modulation configuration, 802.15.4, and Zigbee.

In certain embodiments, the uplink and downlink telemetry transmissions 42, 40 between the IMD 10 and the external communication device 12 follow a telemetry protocol that formulates, transmits and demodulates data packets each comprising a bit stream of modulated data bits. In certain embodiments, the data packets are formulated of a data bit stream with a preamble, data and error checking data bits.

Figure 4:
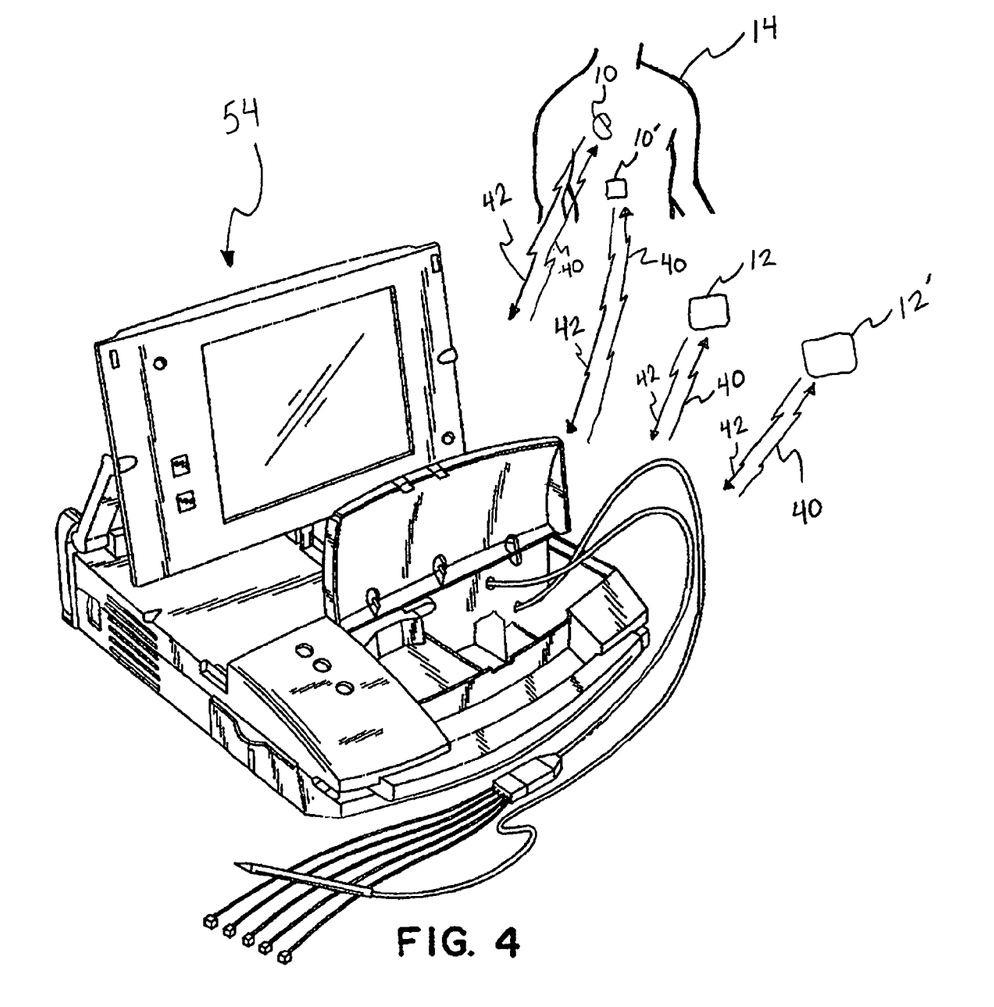
FIG. 4 is a perspective view of an external processing monitor in accordance with certain embodiments of the invention.

In FIG. 4, there is shown a perspective view of an external processing monitor 54 in accordance with certain embodiments of the invention. In certain embodiments, the external processing monitor 54 can be used for bi-directional telemetry communication (via 40, 42) with any of the IMD 10 and other electrical devices (e.g., IMD 10' and the external communication devices 12, 12'). From such telemetry communications 40 and 42, the external processing monitor 54 can be subsequently used to display or further transmit patient data. The external processing monitor 54 generally includes a processing unit (not visibly shown). As should be appreciated, the processing unit can include any of a wide variety of devices. While not being limited to such, the processing unit, in certain embodiments, can be a personal computer type motherboard, e.g., a computer motherboard including a microprocessor and related circuitry such as digital memory. The details of design and operation of the computer system will not be set forth in detail in the present disclosure, as it is believed that such details are well-known to those of ordinary skill in the art. However, such external processing monitor 54 is described in more detail in U.S. Pat. Nos. 5,345,362 and 5,683,432, which patents are incorporated herein by reference in their relevant parts. While not shown, it is to be appreciated that such telemetry communications between the external processing monitor 54 and the IMD 10 and/or any of the other electrical devices (e.g., IMD 10' and/or one or more of the external communication devices 12, 12') can occur in combination with telemetry communications occurring between the IMDs 10, 10' and/or between one or more of the IMDs 10, 10' and one or more of the external communication devices 12, 12' (as exemplified in FIG. 1).

Some of the aforementioned trade-offs or compromises described herein associated with the operational parameters of an RF communication system are generally known in the art. In view of the interrelation of these various parameters of an RF system, including transmission rate, signal-to-noise ratio, energy consumption, etc., embodiments of the present invention contemplate a system in which preprogrammed software and/or one or more additional circuits (e.g., that are preprogrammed, tuned, or fixed) are introduced which enable one or more unique modes of telemetry protocol to be used by the IMD 10, and/or one or more electrical devices (e.g., IMD 10', external communication devices 12, 12') to increase the overall efficiency of the system in light of the above-mentioned trade-offs. As such, the system can be used to achieve one or more of optimizing data transmission, minimizing the risk of interference, and preserving battery energy, such that the system is optimized in terms of performance and/or power consumption while performance goals of the system are still met, as will be hereinafter described in further detail. In certain embodiments, the preprogrammed software and/or additional circuit(s) are incorporated in the IMD internal communication circuit 34 (e.g., in a processor) and similarly disposed in circuitry of the external communication device 12. However, the invention should not be so limited, as it should be appreciated that the software and/or the additional circuit(s) could also be incorporated into the primary circuitry 20 of the IMD 10 (e.g., in the processing unit 30) and/or one of the electrical devices (e.g., IMD 10', external communication devices 12, 12'). It should be further appreciated that the differing functions of the unique modes (enabled by the preprogrammed software and/or additional circuits) may be grouped in different combinations without departing from the spirit of the invention. While the modes are generally described herein with respect to telemetry communications between the IMD 10 and the external communication device 12, it is to be appreciated that such modes can be similarly applied with respect to telemetry communications between IMDs (e.g., between IMD 10 and IMD 10') and to telemetry communications between one or more IMDs (e.g., IMD 10 and/or IMD 10') and a plurality of other electrical devices (e.g., external communication devices 12, 12'), as shown in FIG. 1.

One such unique mode involves maintenance of the telemetry link between the IMD 10 and the external communication device 12. As described herein, the IMD 10 and external communication device 12 are designed to facilitate bi-directional telemetry communication therebetween; however, the potential exists for a variety of problems to crop up in establishing each of these transmission, as discussed below. As is known, such communication generally takes place along uplink and downlink communication channels that are available; however, such channels are generally limited in quantity. As such, all the available channels can be in use by other devices (e.g., other medical devices communicating across these same channels), thereby delaying the desired communication between the IMD 10 and external communication device 12. Further, even if communication across one or more available channels is possible, there is potential for signal integrity to be compromised. By the very nature of establishing use with one of the channels, the signals being sent between the IMD 10 and external communication device 12 are susceptible to partial data loss. This is particularly problematic in environments in which a plurality of IMDs or other medical devices are using telemetry communications channels simultaneously (e.g., clinics, hospitals, nursing homes, etc.).

As such, under a unique mode referenced herein generally as "handshaking" mode, a telemetry link, or communication channel, can be maintained between the IMD 10 and the external communication device 12 at all times. Such link is maintained by continually transmitting "handshaking" signals between the devices across one channel, thereby locking the channel away from being used by other devices. In certain embodiments, the maintenance of the link is facilitated by circuitry within the internal communication circuit 34 of the IMD 10 and/or like circuitry within the external communication device 12. The transmitted "handshaking" signals are generally not used for transmitting patient data, but instead are merely transmitted between the IMD 10 and external communication device 12 to keep one or more communication channels in use. In turn, the "handshaking" signals transmitted are generally short in duration. In certain embodiments, the "handshaking" signals are 1 bit intervals. As such, the continual transmitting of such "handshaking" signals provides an insignificant drain on the electrical energy sources of the IMD 10 and/or external communication device 12.

In certain embodiments, such "handshaking" signals are provided between the IMD 10 and external communication device 12 at a transmission rate that at least maintains the channel for future uplink/downlink transmission signals from the devices. In certain embodiments, the transmission rate of the "handshaking" signals between the IMD 10 and external communication device 12 is sufficiently increased to prevent access by other devices. Such "handshaking" signals can be sent by one or more of the IMD 10 and the external communication device 12. In certain embodiments, the transmission of the "handshaking" signals can be equally shared by the IMD 10 and the external communication device 12. As such, upon either the IMD 10 or external communication device 12 receiving a "handshaking" signal from the other, the receiving device responds in kind by transmitting a return "handshaking" signal at a transmission rate to continue to lock the corresponding communication channel.

Another unique mode involves the transmittance of the data between the IMD 10 and the external communication device 12. As described herein, the IMD 10 is designed to transmit patient data stored therein to the external communication device 12. As is generally known, the transmission of such stored data is a drain on the electrical energy sources of the IMD 10 and external communication device 12. In addition, the integrity and interference resistance of such signals are generally susceptible during such transmissions.

In certain embodiments, to solve the above limitations, the system can be designed to function under a unique mode referenced herein generally as "low transfer rate" mode. As described above, increasing data transmission rate typically requires increasing the bandwidth of the transmitted signals; however, decreasing data transmission rate typically allows for a reduction in the signal bandwidth. With the bandwidth reduced, the power consumption of the electrical energy source as well as the amount of noise that is introduced into the system (i.e., via a decreased signal-to-noise ratio of the transmitted signal) can be generally reduced. With the decreased transmission rate, the potential for successful transmission may be increased.

In addition, in certain embodiments with respect to such "low transfer rate" mode, error checking can be conducted so an increased sampling of the data signals can be provided as the signals are transmitted by the IMD 10 and/or received by the external communication device 12. In certain embodiments, the increased sampling is facilitated by circuitry within the internal communication circuit 34 of the IMD 10. As such, with a reduction in transmission rate, the data signals can be sampled in lower than normal bit time increments while optimizing energy usage.

Also, in certain embodiments, the power consumed during transmission of the patient data can be further reduced. Specifically, during time periods when it is known that either the transmission, reception or both will not be occurring with respect to the IMD 10, one or more portions of the telemetry transceiver 49 of the IMD 10 can be temporarily placed in an "off" state to decrease current drain on the electrical energy source 32. For example, upon interrogation of the IMD 10 and subsequent transmission of the signals via the IMD transmitter 50, the IMD receiver 52 can be placed in an "off" state to decrease current drain on the electrical energy source 32.

Additionally, the power consumed during transmission of the patient data can be reduced using a technique of noise modulation technique similar to amplitude modulation. Generally, modulation schemes (e.g., CDMA) operate above the threshold, yet spread the spectrum out until the power level appears (e.g., on a spectrum analyzer) to be below the noise threshold, or require feedback established at higher power levels (or require other power control mechanisms). Conversely, the noise modulation technique suggested herein attempts to minimize battery power at a level so low that the signal received is just above or slightly below the noise threshold of the receiver such that the signal at the detection circuitry is at or below the noise floor at the detection circuitry. As such, in certain embodiments, the internal communication circuit 34 can be programmed so as to keep one or more portions of the IMD receiver 52 in an "active" state during transmission. In turn, such portions of the receiver 52 can be used to receive feedback (e.g., from the external communication device 12) based on the relation of the data signals previously transmitted with the general noise threshold of the external communication device 12. Ideally, the IMD 10 is designed to operate as close to the general noise threshold as possible. As such, in certain embodiments, the internal communication circuit 34 of the IMD 10 can adjust its telemetry transmissions accordingly based on the feedback attained by the IMD receiver 52. This technique is also beneficial because it generally improves signal security and reduces potential for causing interference.

A further unique mode also involves the transmittance of the data between the IMD 10 and the external communication device 12. As described herein, the IMD 10 can be designed to store patient data upon certain events occurring within the patient or upon manual triggering by the patient 14. Subsequently, the stored patient data can be transmitted upon the IMD 10 being triggered (e.g., by the external communication device 12). However, the IMD memory unit 28 is limited as to the amount of data that can be stored. As such, the IMD 10 can be designed to either overwrite the previously stored data or transmit the stored data upon the memory unit 28 reaching its capacity. However, continual transmittal of the stored data has potential of causing a significant drain on the IMD electrical energy source 32.

In certain embodiments, to solve the above limitations, the system can be designed to function under a unique mode referenced herein generally as "data burst" mode, in which stored patient data is transmitted from the IMD 10 in data bursts. In certain embodiments, this "data burst" type of telemetry transmission would use a loop recorder, e.g., contained in the internal communication circuit 34. The implementation of such loop recorder would be most advantageous when IMDs are used which record patient data over long time durations. One such IMD is the Medtronic® REVEAL® Insertable Loop Recorder, which can generally be called upon to capture patient data for durations at least ranging from twenty-four to forty-eight hours.

In certain embodiments of the "data burst" mode, the internal communication circuit 34 of the IMD 10 can be designed to communicate the patient data using multiple carriers. In turn, the patient data can be sent in a shorter time duration by transmitting different sets of the data over different frequencies. Generally, this could be accomplished by using any modulation type or technique in which frequency division multiplexing or other techniques are used to create multiple distinct spectrums of modulated data. One exemplary modulation type is Orthogonal Frequency Division Multiplexing (OFDM); however, as described above, the invention should not be limited to such.

Another unique mode further involves the transmittance of the data between the IMD 10 and the external communication device 12. As described herein, stored patient data can be transmitted from the IMD 10 upon triggering of the IMD 10 by the external communication device 12. As described herein, the stored patient data is generally transmitted in packets, and there is potential for these packets to collide with other signals and become lost. With the loss of such packets, the signal integrity of the patient data recovered by the external communication device 12 is compromised.

In certain embodiments, to solve the above limitations, the system can be designed to function under a unique mode referenced herein generally as "random access protocol" mode, in which the amount of time between transmissions from the IMD 10 is varied by a random amount of time, thereby reducing the probability of interference. In certain embodiments, such techniques for randomization of the patient data transmissions can be programmed within processing circuitry of the internal communication circuit 34 of the IMD 10 and like circuitry within the external communication device 12. In certain embodiments, such techniques can be similar to the techniques employed by ALOHA systems, as will now be described.

As a background, ALOHA systems generally have a number of broadcasting stations communicating with a single receiving station, with the broadcasting stations transmitting at random intervals. In the ALOHA system, collisions can occur so that messages are lost. However, the solution employed by such systems is to monitor the retransmission of the information from the receiving station so that each broadcasting station can be made aware of when the transmission has been lost. Each broadcasting station is then programmed to retransmit the lost information after a predetermined generally pseudorandom period of time. The ALOHA systems requires retransmission of the information from the receiving station to take place substantially immediately and requires each broadcasting station to also have a receiving capability.

In light of the ALOHA systems, in certain embodiments, the IMD 10 would take the place of the broadcasting stations and the external communication device 12 would take the place of the receiving station. As such, when collisions occur, resulting in the loss of transmitted patient data, the external communication device 12 would monitor the retransmission of the patient data so that the IMD 10 can be made aware (i.e., from the external monitor 12) when the transmission has been lost. The internal communication circuit 34 of the IMD 10 is then programmed to retransmit the lost information after a predetermined generally pseudorandom or random period of time. In accordance with such implementation, the retransmission of the patient data from the IMD 10 can take place either substantially immediately or randomly following the initial patient data transmission being lost.

As mentioned above, the specific modes of the telemetry protocol described herein are developed to optimize the transfer of data between devices, minimize the risk of interference, and preserve battery energy. By fitting the mode to the corresponding scenario, performance enhancements can be realized for the telemetry system which can be used to reduce system costs or optimize performance at the expense of additions made to the IMD either in the software for the IMD 10 (e.g., implemented in the internal communication circuit 34) and/or one or more additional circuits that can implement aspects of the RF circuitry and protocol in hardware/firmware in the IMD 10.

Figure 5:
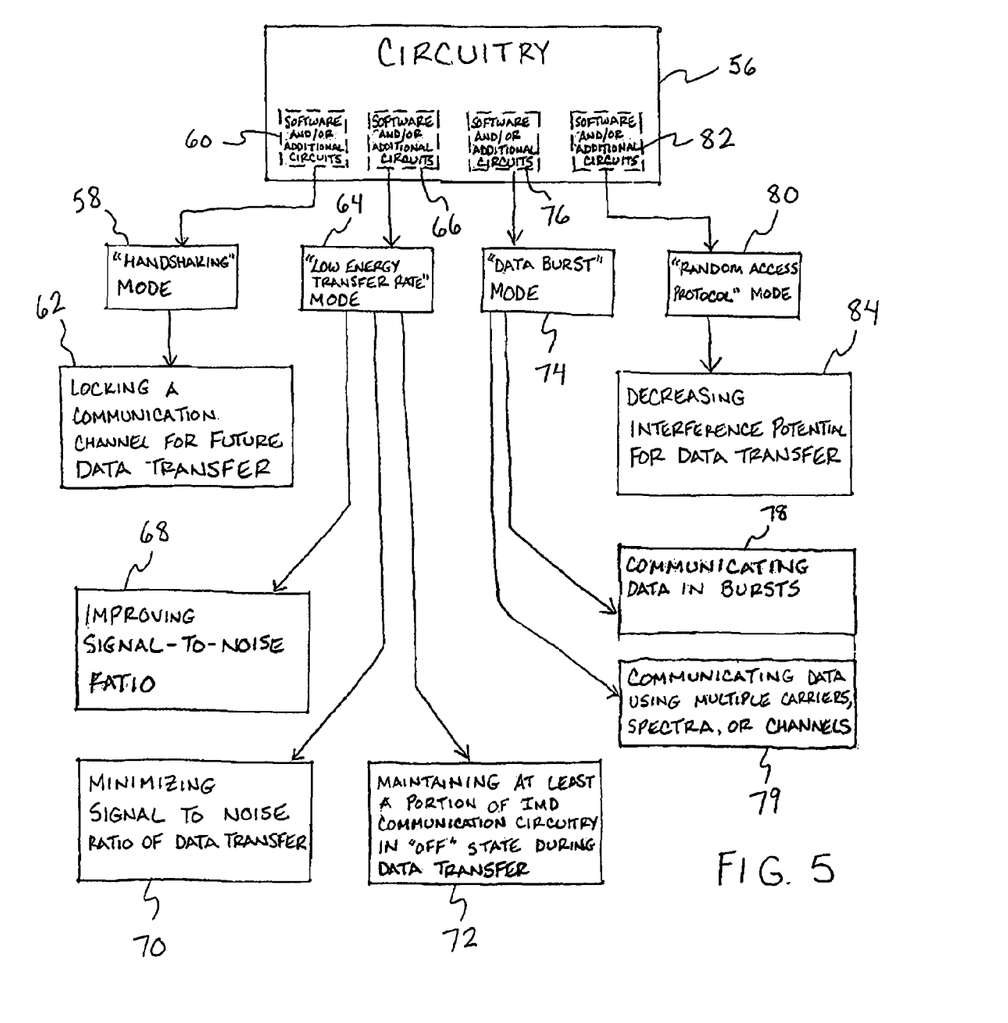
FIG. 5 is a block diagram of specific modes of telemetry protocol in accordance with certain embodiments of the invention.

FIG. 5 shows a block diagram illustrating the specific modes of the telemetry protocol detailed above in accordance with certain embodiments of the invention. As shown, circuitry 56 within one or more of the IMD 10 and the external communication device 12 (shown in FIG. 1) exists which is configured to implement one or more of the modes of protocol for the telemetry communications between the IMD 10 and the external communication device 12. As described above, the one or more modes of protocol are configured to provide one or more of optimizing transfer of data between the IMD 10 and the external communication device 12, minimizing interference of the data transfer, and preserving electrical energy sources of the IMD 10 and the external communication device 12.

A first mode of protocol involves a "handshaking" mode 58 being enabled via software (preprogrammed in the circuitry 56) and/or one or more additional circuits 60. The software and/or one or more additional circuits 60 are configured to provide a function 62 of controlling the one or more of the IMD and external communication device transmitter and/or receiver units 49 and 45 respectively (shown in FIG. 3) to transmit handshaking signals therebetween, enabling a communication channel to be locked for future data transfer between the IMD 10 and the external communication device 12. A second mode of protocol involves a "low transfer rate" mode 64 being enabled via software (preprogrammed in the circuitry 56) and/or one or more additional circuits 66. The software and/or one or more additional circuits 66 are configured to provide one or more of the following: a function 68 of lowering rate of the data transfer between the IMD 10 and the external communication device 12 which enables improved Signal-to-Noise Ratio (SNR), a function 70 of controlling the IMD transmitter and/or receiver unit 49 to receive feedback from the external communication device 12 during the data transfer and use such feedback to minimize SNR of the data transfer, and a function 72 of maintaining one or more portions of the transmitter and/or receiver unit 49 in an "off" state during data receipt and/or transfer to conserve the IMD electrical energy source 32 (shown in FIG. 2).

A third mode of protocol involves a "data burst" mode 74 being enabled via software (preprogrammed in the circuitry 56) and/or one or more additional circuits 76. The software and/or one or more additional circuits 76 are configured to provide one or more of the following: a function 78 of conserving the IMD electrical energy source 32 (shown in FIG. 2) by providing the data transfer between the IMD 10 and the external communication device 12 in bursts over lengths of time during which a recorder (e.g., a loop recorder) used in conjunction with the IMD memory unit 28 (shown in FIG. 2)

reaches capacity, and a function 79 of conserving the IMD electrical energy source 32 by providing the data transfer using multiple carriers, spectra, or channels. A fourth mode of protocol involves a "random access protocol" mode 80 being enabled via software (preprogrammed in the circuitry 56) and/or one or more additional circuits 82. The software and/or one or more additional circuits 82 are configured to provide a function 84 of controlling the IMD and external communication device transmitter and/or receiver units 49 and 45 respectively (shown in FIG. 3) to facilitate a randomization of the data transfer duty cycle to decrease interference potential for the data transfer. It is to be appreciated that the "data burst" mode 74 can be triggered by a variety of means, including but not limited to signaling from the external communication device 12 or from a magnet (not shown) being swiped proximate to the IMD 10 by the patient 14.

It should be appreciated that the software and/or one or more additional circuits 60, 66, 76, and 82 can be combined as a single software or a single additional circuit without departing from the spirit of the invention. Likewise, it should also be appreciated that the software and/or one or more additional circuits 60, 66, 76, and 82 can be configured differently to provide for different combinations of any of the functions 62, 68, 70, 72, 78, 79, and 84 described above. As such, instead of the modes 58, 64, 74, and 80 identified above, the different combinations of the functions 62, 68, 70, 72, 78, 79, and 84 can be identified in any way desired. For example, instead of the modes 58, 64, 74, and 80 identified above, the functions 62, 68, 70, 72, 78, 79, and 84 can be grouped and identified with respect to one or more of optimizing transfer of data between the IMD 10 and the external communication device 12, minimizing interference of the data transfer, and preserving electrical energy sources of the IMD 10 and the external communication device 12.

It will be appreciated the embodiments of the present invention can take many forms. The true essence and spirit of these embodiments of the invention are defined in the appended claims, and it is not intended the embodiment of the invention presented herein should limit the scope thereof.

What is claimed is:

1. A system for telemetry communication involving multiple medical devices comprising:
   an implantable medical device:
      configured to communicate data over a communication channel during telemetry communications sessions using at least one of a handshaking mode and a low transfer rate mode for each of the telemetry communication sessions, the handshaking mode being configured to communicate over a first bandwidth and the low transfer rate mode being configured to communicate over the first bandwidth and a second bandwidth narrower than the first bandwidth;
      wherein at least one of the handshaking mode and the low transfer rate mode have a plurality of modulation schemes which modulate data transmitted during the telemetry communications sessions; and
      comprising circuitry configured to select one of the at least one of the handshaking mode and the low transfer rate mode and, if the one of the at least one of the handshaking mode and the low transfer rate mode has a plurality of modulation schemes, selecting one of the plurality of modulation schemes; and
   a plurality of electrical devices, each of the electrical devices being configured to enable telemetry communications with the implantable medical device using one of the at least one of the handshaking mode and the low transfer rate mode between that particular electrical device and the implantable medical device for each telemetry communication session; and
   wherein the handshaking mode is configured to maintain the communication channel between the implantable medical device and one of the plurality of electrical devices by locking the communication channel by transmitting handshaking signals not used, for transmitting patient data.

2. The system of claim 1, wherein the implantable medical device comprises a cardiac device.

3. The system of claim 1, wherein the plurality of electrical devices comprise at least one medical instrumentation implanted in the patient and at least one external communication device.

4. The system of claim 3, wherein the at least one medical instrumentation comprises one or more of a drug delivery pump, a stimulator, a physiologic monitor, a recorder, an implant, and an artificial organ.

5. The system of claim 3, wherein the at least one external communication device comprises one or more of a portable programmer, an interrogator, a recorder, a monitor, and a telemetered signals transceiver.

6. The system of claim 1, wherein the circuitry comprises a processing unit.

7. The system of claim 1, wherein at least one of the plurality of modulation schemes is one of noise modulation, general spread spectrum encoding, bi-phase encoding, Frequency Shift Key (FSK), Time Division Multiple Access (TDMA), pre-emphasis/de-emphasis of baseband, vestigial, Code Division Multiple Access (CDMA), Quadrature Amplitude Modulation (QAM), pi/8, Quad-QAM, 256-QAM, 16-QAM, delta modulation, Phase Shift Key (PSK), Quadrature Phase Shift Keying (QPSK), Quadrature Amplitude Shift Keying (QASK), minimum shift keying, Tamed Frequency Modulation (TFM), Orthogonal Frequency Division Multiplexing (OFDM), BLUETOOTH communication protocol, any 802.11 modulation configuration, Worldwide Interoperability for Microwave Access (WiMAX), any 802.16 modulation configuration, 802.15.4, and Zigbee.

8. The system of claim 1, wherein the data comprises one or more of stored physiologic data, real-time generated physiologic data, and non-physiologic data.

9. The system of claim 1, further comprising an external processing monitor configured to enable telemetry communications with the implantable medical device and the plurality of electrical devices.

10. The system of claim 1, wherein the handshaking mode is enabled via software preprogrammed in the circuitry and circuits of the circuitry, and wherein the software and circuits are configured to control the implantable medical device and the one of the plurality of electrical devices to periodically transmit the handshaking signals therebetween enabling the communication channel to be locked prior to transferring the data.

11. The system of claim 1, wherein the low transfer rate mode is enabled via software preprogrammed in the circuitry and circuits of the circuitry, and wherein the software and circuits are configured to provide one or more of the following:
   lower rate of transferring the data enabling increased Signal-to-Noise Ratio,
   control the implantable medical device unit to receive feedback from the one of the plurality of electrical devices during the data transfer and use the feedback for noise modulation of the data, and
   maintain a portion of the implantable medical device in an "off" state during one or more of data receipt and transfer to conserve an electrical energy source of the implantable medical device.

12. The system of claim 1, wherein the implantable medical device is further configured to enable telemetry communications using a data burst mode enabled via software preprogrammed in the circuitry and circuits of the circuitry, and wherein the software and circuits are configured to provide one or more of the following:
   transfer the data in bursts over lengths of time during which a recorder used in conjunction with a memory unit of the implantable medical device reaches capacity, and
   transfer the data using a modulation technique in which multiple distinct spectrums are used for modulated data.

13. The system of claim 12, further comprising a loop recorder within the circuitry, wherein the loop recorder is configured to store the data prior to the data transfer.

14. The system of claim 1, wherein the implantable medical device is further configured to enable telemetry communications using a random access protocol mode enabled via software preprogrammed in the circuitry and circuits of the circuitry, and wherein the software and circuits are configured to control the implantable medical device and the at one of the plurality of electrical devices to facilitate a randomization of the data decreasing potential of interference with the data.

15. The system of claim 14, wherein the randomization comprises the process used in ALOHA networks.

16. The system of claim 1 wherein the circuitry selects the one of the handshaking mode and the low transfer rate mode for each one of the telemetry communication sessions based, at least in part, on at least one of a transmission rate, ambient noise and energy consumption.

17. A system for optimizing telemetry communication involving multiple medical devices comprising:
   an implantable medical device:
      configured to communicate data over a communication channel during telemetry communications sessions using at least one of a handshaking mode and a low transfer rate mode for each of the telemetry communication sessions, the handshaking mode being configured to communicate over a first bandwidth and the low transfer rate mode being configured to communicate over the first bandwidth and a second bandwidth narrower than the first bandwidth;
      wherein at least one of the handshaking mode and the low transfer rate mode have a modulation scheme which modulates data transmitted during the telemetry communications sessions; and
      comprising circuitry configured to select one of the at least one of the handshaking mode and the low transfer rate mode and, if the particular one of the multiple modes of protocol has the modulation scheme, apply the modulation scheme;
   an electrical device configured to enable telemetry communications with the implantable medical device using one of the at least one of the handshaking mode and the low transfer rate mode between the electrical device and the implantable medical device for each telemetry communication session; and
   wherein the handshaking mode is configured to maintain the communication channel between the implantable medical device and the electrical device by locking the communication channel by transmitting handshaking signals not used for transmitting patient data.

18. The system of claim 17, wherein the circuitry has optimizing software preprogrammed therein and additional circuits, and wherein the optimizing software and additional circuits are configured to optimize one of the telemetry communications sessions by one or more of the following:
   controlling the implantable medical device and the electrical device to transmit handshaking signals therebetween according to the handshaking mode,
   lowering rate of the data transfer enabling increased Signal-to-Noise Ratio according to the low transfer rate mode,
   transferring the data in bursts over lengths of time during which a recorder used in conjunction with a memory unit of the implantable medical device reaches capacity, and
   transferring the data using the plurality of modulation schemes in which multiple distinct spectrums are used for modulated data.

19. The system of claim 17, wherein the circuitry has interference minimizing software preprogrammed therein and additional circuits, and wherein the interference minimizing software and additional circuits are configured to minimize interference of one of the telemetry communications sessions by one or more of the following:
   controlling the implantable medical device to receive feedback from the electrical device during a telemetry communications session and use the feedback for noise modulation of the one of the telemetry communications sessions according to the low transfer rate mode, and
   controlling the implantable medical device and the electrical device to facilitate a randomization of the one of the telemetry communications sessions.

20. The system of claim 17, wherein the circuitry has energy conserving software preprogrammed therein and additional circuits, and wherein the energy conserving software and additional circuits are configured to conserve an electrical energy source of the implantable medical device by one or more of the following:
   maintaining a portion of the implantable medical device, in an "off" state during data receipt and transfer to conserve the electrical energy source of the implantable medical device according to the low transfer rate mode, and
   providing one of the telemetry communications sessions in bursts over lengths of time during which a memory unit of the implantable medical device reaches capacity.

21. A method of optimizing telemetry communication involving multiple medical devices comprising:
   providing an implantable medical device, the implantable medical device:
      configured to communicate data over a communication channel during telemetry communications sessions using at least one of a handshaking mode and a low transfer rate mode for each of the telemetry communication sessions, the handshaking mode being configured to communicate over a first bandwidth and the low transfer rate mode being configured to communicate over the first bandwidth and a second bandwidth narrower than the first bandwidth;
      wherein at least one of the handshaking mode and the low transfer rate mode have a modulation scheme which modulates data transmitted during the telemetry communications sessions; and
      comprising circuitry configured to select one of the at least one of the handshaking mode and the low transfer rate mode and, if the one of the at least one of the handshaking mode and the low transfer rate mode has a plurality of modulation schemes, apply the modulation scheme; and
   providing a plurality of electrical devices configured to enable telemetry communications with the implantable medical device using one of the at least one of the handshaking mode and the low transfer rate mode for each telemetry communication session; and wherein the handshaking mode is configured to maintain the communication channel between the implantable medical device and one of the plurality of electrical devices by locking the communication channel by transmitting handshaking signals not used for transmitting patient data.

* * * * *